United States Patent [19]
Fried et al.

[11] Patent Number: 5,608,107
[45] Date of Patent: Mar. 4, 1997

[54] PREPARATION OF ALKOXYALKANOIC ACIDS

[75] Inventors: Herbert E. Fried; David M. Singleton, both of Houston, Tex.

[73] Assignee: Shell Oil Company, Houston, Tex.

[21] Appl. No.: 455,369

[22] Filed: May 31, 1995

[51] Int. Cl.$^6$ .................................................. C07C 51/235
[52] U.S. Cl. .................... 562/538; 562/540; 562/418; 562/419; 562/420
[58] Field of Search .................................. 562/418, 419, 562/420, 538, 540, 537

[56] References Cited

U.S. PATENT DOCUMENTS

| | | | |
|---|---|---|---|
| 3,998,924 | 12/1976 | Jones et al. | 423/7 |
| 4,348,509 | 9/1982 | Sanders et al. | 562/538 |
| 4,620,033 | 10/1986 | Isshiki et al. | 562/519 |
| 5,136,101 | 8/1992 | Fried | 568/402 |
| 5,136,102 | 8/1992 | Fried | 568/402 |
| 5,136,103 | 8/1992 | Fried | 568/402 |
| 5,155,278 | 10/1992 | Fried | 568/471 |
| 5,155,279 | 10/1992 | Fried | 568/471 |
| 5,155,280 | 10/1992 | Fried | 568/471 |
| 5,162,579 | 11/1992 | Fried | 562/537 |
| 5,166,422 | 11/1992 | Fried | 562/537 |
| 5,166,423 | 11/1992 | Fried | 562/537 |
| 5,175,359 | 12/1992 | Fried | 562/537 |
| 5,175,360 | 12/1992 | Fried | 562/538 |
| 5,179,218 | 1/1993 | Fried | 554/134 |
| 5,239,116 | 8/1993 | Fried | 562/537 |
| 5,387,712 | 2/1995 | Fried | 562/420 |

FOREIGN PATENT DOCUMENTS 5096516 7/1975 Japan.

OTHER PUBLICATIONS

Miyazawa et al., "Oxidation of Benzyl Alcohol with Iron (III) Using Polymers Containing Nitroxyl Radical Structure as a Mediator, " J. Polym. Sci., Polym. Chem. Ed., 23(9), 1985, pp. 2487–2494. Abstract.

Miyazawa et al., "Oxidation of Benzyl Alcohol with Copper (II) Mediated by a Polymeric Oxoaminium Salt, " J. Mol. Catal., 49(1), 1988, 131–134. (Abstract only).

Ganem et al., "Biological Spin Labels as Organic Reagents. Oxidation of Alcohols to Carbonyl Compounds Using Nitroxyls, " J. Org. Chem., 40(13), 1975, pp. 1998–2000.

Miyazawa et al., "Oxidation of Benzyl Alcohol by Iron(III) Mediated by Nitroxyl Radical. " J. Mol. Catal., 31(2), 1985, pp. 217–220.

Annelli et al., "Fast and Selective Oxidation of Primary Alcohols to Aldehydes or to Carboxylic Acids and of Secondary Alcohols to Ketones Mediated by Oxoammonium Salts under Two–Phase Conditions, " J. Org. Chem., 52(12), 1987, pp. 2559–2562.

Inokuchi et al., "A Selective and Efficient Method for Alcohol Oxidations Mediated by N–Oxoammonium Salts in Combination with Sodium Bromite, " J. Org. Chem., 1990, 55 pp. 462–466.

Organic Synthesis, vol. 69, p. 212 (1990).

Semmelhack et al., "Oxidation of Alcohols to Aldehydes with Oxygen and Cupric Ion, Mediated by Nitrosonium Ion, " J. Am. Chem. Soc., 1984, 106, 3374–376.

Yamaguchi et al., "Application of Redox System Based on Nitroxides to Organic Synthesis, " Pure & Applied Chemistry, vol. 62(2), 1990, 217–222.

E. S. Kagan et al., "Chemistry of Hindered Amines from the Piperidine Series", Synthesis, 1984, pp. 895–916.

R. M. Dupeyre et al., "Nitroxides. XIX. Norpseudopelletierine–N–oxyl, a New, Stable, Unhindered Free Radical, " JACS, 88 (13), 1966, pp. 3180–3181.

E. G. Rozantsev et al., "Synthesis and Reaction of Stable Nitroxyl Radicals I. Synthesis" Synthesis, Apr. 1971, pp. 190–202.

E. G. Rozantsev et al., "Synthesis and Reaction of Stable Nitroxyl Radicals II. Reactions, " Synthesis, Apr. 1971, pp. 401–414.

*Primary Examiner*—Gary Geist
*Assistant Examiner*—Rosalynd A. Williams
*Attorney, Agent, or Firm*—Pamela J. McCollough

[57] ABSTRACT

A process for preparing an alkoxyalkanoic acid by reacting the corresponding alkoxyalkanol with a resin-supported stable free radical nitroxide in the presence of a chlorine-containing oxidant and a solvent at a temperature in the range of from about 0° C. to about 35° C. and thereafter separating out the alkoxyalkanoic acid.

11 Claims, No Drawings

PREPARATION OF ALKOXYALKANOIC ACIDS

FIELD OF THE INVENTION

This invention relates to a process for the preparation of alkoxyalkanoic acids by the oxidation of the corresponding alkoxyalkanols in the presence of a resin-supported stable free radical nitroxide and a chlorine-containing oxidant and a solvent.

BACKGROUND OF THE INVENTION

Alkoxyalkanoic acids are useful as anionic surfactants or emulsifying agents. These acids, being composed of only the elements C, H and O, do not pose the environmental problems that other detergents containing heteroatoms such as N, S, and P pose. The alkoxyalkanoic acids can be prepared in a two-step process of first reacting an alkanol with an alkoxylate and a suitable alkoxylation catalyst and thereafter converting the resultant alkoxyalkanol to the alkoxyalkanoic acid.

It is also known to convert alkoxyalkanols such as methyl carbitol to the corresponding carboxylic acids by oxidizing them with nitric acid. However, relatively large amounts of nitric acid are required and not all of the nitric acid can be separated by distillation. In addition, cleavage of the ether linkages occurs to a large degree during this process.

Japanese Patent No. 50-96516, issued Jul. 31, 1975, discloses a process for the preparation of carboxylic acid salts by the liquid phase dehydrogenation of alcohols with caustic alkali in the presence of precious metal catalysts, including palladium. This process uses a relatively high temperature, 100° C.–270° C. These high temperatures can degrade the ether linkages especially in the highly ethoxylated alcohols.

It is known to use nitroxyl radicals/oxoammonium salts in the oxidation of primary alcohols to produce aldehydes and acids and secondary alcohols to ketones. *Journal of Organic Chemistry*, Vol. 52(12), pp. 2559–2562; *Pure and Applied Chemistry*, Vol. 62(2), 1990, pp. 217–222; *Journal of Organic Chemistry*, Vol. 55, 1990, pp. 462–466. The primary products produced in these processes are aldehydes and the stoichiometrically consumed oxidant is hypochlorite.

It is generally more difficult to oxidize alkoxyalkanols than alkanols as it is difficult to oxidize alkoxyalkanols without splitting the molecular chain at the ether linkage and thereby produce a large proportion of undesired by-product. It would therefore be advantageous to produce alkoxyalkanoic acids in high yields and with high selectivities without producing large amounts of other products such as aldehydes, esters, and alkanoic acids. It would also be advantageous to have a supported nitroxide to make separation of the product easier and to enable the supported nitroxide to be isolated and reused.

It has been found that alkoxyalkanoic acids having high selectivities can be produced without forming highly corrosive, difficult to separate, side-products by using catalytic amounts of a resin-supported stable free radical nitroxide, a chlorine-containing oxidant and a solvent.

SUMMARY OF THE INVENTION

This invention relates to a process for preparing an alkoxyalkanoic acid by reacting the corresponding alkoxyalkanol with a resin-supported stable free radical nitroxide in the presence of a chlorine-containing oxidant and a solvent at a temperature in the range of from about 0° C. to about 35° C. and thereafter separating out the alkoxyalkanoic acid.

In particular, this invention relates to a process for the preparation of an alkoxyalkanoic acid of the formula

wherein R is a primary alkyl, secondary alkyl, tertiary alkyl, aromatic or an alkyl aromatic group having from 1 to about 1000 carbon atoms, R' is hydrogen, alkyl, aryl or mixtures thereof (on the individual molecule) and n is an integer of from 1 to about 1000 which comprises reacting the corresponding alkoxyalkanol with a resin-supported stable free radical nitroxide having the formula:

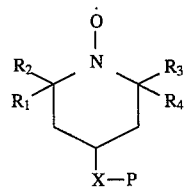

wherein each of $R_1$, $R_2$, $R_3$, and $R_4$ is an alkyl, aryl or substituted alkyl group having 1 to about 15 carbon atoms, X is selected from the group consisting of

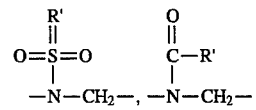

wherein R' is an alkyl, aryl, or amido,

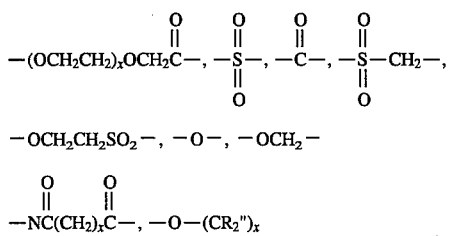

wherein R" is alkyl or hydrogen, and P is a polystyrene, in the presence of a chlorine-containing oxidant and a solvent at a temperature in the range of from about 0° C. to about 35° C. and thereafter separating out the alkoxyalkanoic acid.

DESCRIPTION OF THE PREFERRED EMBODIMENTS

The present process converts alkoxyalkanols of the formula

    (I)

wherein R is a primary alkyl, secondary alkyl, tertiary alkyl, aromatic or an alkyl aromatic group having preferably 1 to about 1000; more preferably about 11 to about 18 carbon atoms, R' is hydrogen, alkyl, aryl or mixtures thereof (on the individual molecule) and n represents the average number of oxyalkylene groups and is an integer of from 1 to about 1000, preferably from about 2 to about 9, to the corresponding alkoxyalkanoic acids of the formula:

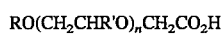    (II)

by contacting the alkoxyalkanol with a resin-supported stable free radical nitroxide in the presence of a chlorine-containing oxidant and a solvent at a temperature in the range of from about 0° C. to about 35° C. and thereafter separating out the alkoxyalkanoic acid. The alkyl group, R, in the above formula I can be substituted with any substituent which does not interfere with the oxidation of the hydroxy group. Such substituents include —OR", —CH$_3$, —COOH, CONH$_2$ and COOR' wherein R' is an alkyl or aryl group.

The process of the instant invention is particularly suited to ethoxylated, or propoxylated alcohols with alkyl chains (R) of about 8 to about 20, preferably of about 11 to about 18 carbon atoms. The R' groups on an individual molecule can be hydrogen, alkyl, aryl or mixtures thereof. For example, straight ethoxylated, straight propoxylated and mixed ethoxylated-propoxylated detergent alcohols are available. The number of such alkoxylate groups, (CH$_2$CHR'O), typically ranges from about 1 to about 1000. Commercially, detergent range ethoxylated alcohols are available with an average of 3, 7, 9 and 12 ethoxylate units per molecule. Others can be readily prepared. In a preferred embodiment, the starting alkoxyalkanol is an ethoxylated alcohol which has had the unreacted alcohols and lower ethoxylates topped off in order to give an ethoxylated alcohol having about 3 to about 4 ethylene oxide units per molecule.

The term "stable free radical nitroxide" as used herein shall mean a free radical nitroxide or nitroxyl that can be prepared by conventional chemical methods and will exist long enough to be used in a subsequent chemical reaction or examined in a static system by normal methods of spectroscopy. Generally, the stable free radical nitroxides of the present invention have a half life of at least one year. The term "stable free radical" shall also be understood to include the precursor to a stable free radical from which the stable free radical may be produced in-situ.

The stable free radical nitroxides, as used in the present process, are precursors to catalysts, i.e., oxoammonium salts, active for the oxidation of alkoxyalkanols to the corresponding acids. These catalysts are generated in situ by the oxidation of a stable free radical nitroxide to an oxoammonium salt. The stable free radical nitroxide can be obtained by the oxidation of secondary amines or hydroxylamines.

The stable free radical nitroxides which are suitable for use in the instant invention are those which are bound to or supported on a resin P with a linkage of X and have the formula:

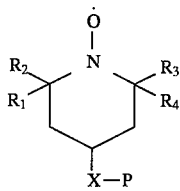  (III)

wherein each of R$_1$, R$_2$, R$_3$ and R$_4$ is an alkyl, aryl or substituted alkyl group and no hydrogen is bound to the remaining valences of the carbon atoms bound to the nitrogen. In the above formula III, X is selected from the group consisting of

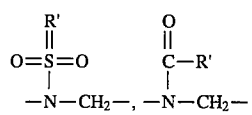

wherein R' is an alkyl, aryl, or amido,

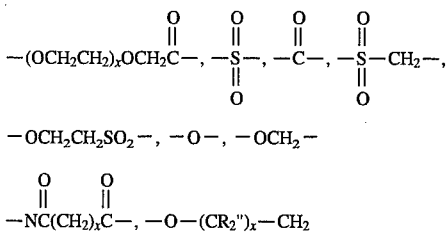

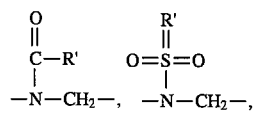

wherin R" is alkyl or hydrogin, with and —O—(CR$_2$")$_x$—CH$_2$ being preferred and P is a polystyrene. As used herein the term "alkyl" is meant to include cycloalkyl. The alkyl (or heteroatom substituted) groups R$_1$, R$_2$, R$_3$ and R$_4$ may be the same or different, and preferably contain 1 to 15 carbon atoms. Preferably, R$_1$, R$_2$, R$_3$ and R$_4$ are methyl, ethyl, or propyl groups. In addition to hydrogen, the heteroatom substituents may include, halogen, oxygen, nitrogen and the like, as long as such substituents do not interfere with the oxidation reaction.

In a preferred embodiment, the resin-supported stable free radical nitroxide is a resin-supported 2,2,6,6-tetramethyl-piperidin-1-oxyl, i.e. resin-supported 2,2,6,6-tetramethyl-1-piperidinyloxy, having the formula:

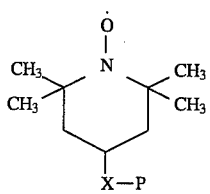  (IV)

The stable free radical nitroxide is supported on a resin, P, with a linkage, X. Particularly suitable resins include those which are 1–2% cross-linked with divinylbenzene and which contain 1–4 milliequivalents per gram (meg/g) of benzylic chloride. Resins such as Merrifield's resin, which is comprised of chloromethylated polystyrene are particularly preferred. The resin supported nitroxides are typically prepared by contacting a hydroxy-containing and/or an amine-containing stable free radical nitroxide with chloromethylated polystyrene in the presence of a solvent such as, for example, dimethylformamide, at temperatures in the range of from about 20° C. to about 135° C. In the case of the amine-containing stable free radical nitroxide, the resulting product is then acetylated with acetic anhydride in order to provide a resin-supported nitroxide which is suitable for use in the present invention and which gives a linkage which is stable under oxidative reaction conditions.

Suitable linkages, X, are those which, as set forth above, are stable under oxidative reaction conditions. Suitable linkages include the group consisting of

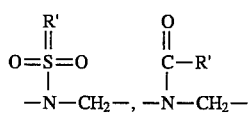

wherein R' is an alkyl, aryl, or amido,

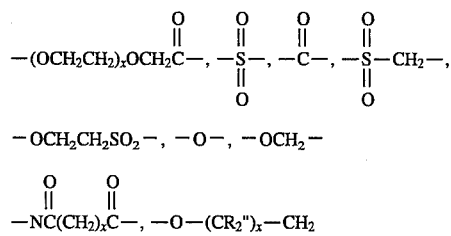

wherein R" is alkyl or hydrogen. In a preferred embodiment, the linkage is selected from

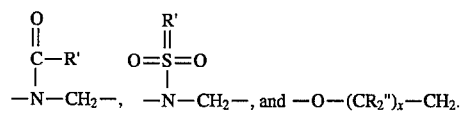

The chlorine-containing oxidants suitable for use in the present invention are those compounds which are capable of oxidizing the resin-supported stable free radical nitroxide to the oxoammonium salt. Suitable chlorine-containing gases oxidants include chlorine, hypochlorite and N-chloro compounds, with chlorine and hypochlorite being preferred. Suitable hypochlorite oxidants include sodium hypochlorite, which is typically used in an aqueous solution having a concentration of up to about 10%, preferably from about 2.5% to about 5%. When chlorine is used as the oxidant, chlorine is suitably bubbled into the reaction solution.

The reaction of the instant invention is carried out utilizing a resin-supported stable free radical nitroxide. The solvent is typically a nonaqueous solvent which is to a large extent immiscible in water, but in which the alkoxyalkanol is readily soluble. Solvents which are most suitable are those having dielectric constants greater than about 2. The solvent may be added to the reaction mixture, or alternatively, the nitroxide may be dissolved in the solvent prior to addition of the nitroxide to the reaction medium. The solvent is typically selected from the group consisting of ethyl acetate, dichloromethane, acetonitrile, chlorobenzene, toluene, xylene, carbon tetrachloride, chloroform, dichloroethylene, tetrachloroethylene, diethyl ether, methyl-tert-butyl ether and mixtures thereof. In a preferred embodiment, the solvent is selected from the group consisting of ethyl acetate, dichloromethane and mixtures thereof. The ratio of solvent to starting alkoxyalkanol utilized in the process is typically in the range of from about 20:1 to about 0.5:1 and preferably in the range of from about 5:1 to about 1:1.

The amounts and concentrations of the reactants utilized in the process of the instant invention can vary within wide ranges. The amount of resin-supported stable free radical nitroxide utilized depends on the manner in which the reagents are contacted. The chlorine-containing oxidant is typically added last, i.e., the chlorine-containing oxidant is added slowly to a reaction mixture containing alkoxylalkanol, solvent and nitroxide. When this procedure is used, the amount of stable free radical nitroxide is typically in the range of from about 500 parts per million to about 30,000 parts per million, preferably from about 1,000 parts per million to about 10,000 parts per million, and more preferably from about 1,000 parts per million to about 4,000 parts per million, basis the weight of the starting alkoxyalkanol. Alternatively, the chlorine-containing oxidant may be added prior to the addition of the nitroxide, in which case the amount of nitroxide utilized will typically be in the range of from about 100 parts per million to about 3,000 parts per million, basis the weight of the starting alkoxyalkanol. Generally, the amount of chlorine-containing oxidant used is in the range of from about 2 equivalents to about 3 equivalents, preferably from about 2 to about 2.5 equivalents, basis the number of moles of alkoxyalkanol.

The reaction is suitably begun in a neutral to slightly basic medium. If the reaction is conducted in a medium which is initially too basic, the start of the oxidation reaction will be extremely slow and lead to longer reaction times. If the reaction is conducted in a medium which is buffered and is too basic, the oxidation reaction will be extremely slow and lead to low conversion of the alkoxyalkanol to the corresponding acid. On the other hand, if the reaction medium is too acidic, the reaction may result in higher amounts of esters than is desirable. Thus, in one embodiment, a buffer such as, for example, sodium bicarbonate, is added to the reaction mixture, or to the sodium hypochlorite solution, either at the beginning of the reaction or after partial completion of the reaction to adjust the pH to a value of about 8–9. Alternatively, an acid is added to the reaction mixture either at the beginning of the reaction or after partial completion of the reaction to adjust the pH to a value of about 8–9. Suitable acids include hydrochloric acid, sulfuric acid, phosphoric acid and the like. Alternatively, the pH of the reaction mixture may be adjusted by recycling alkoxyalkanoic acid produced according to the invention. The concentration of the acid will typically be in the range of from about 1% to about 20%, preferably in the range of from about 1% to about 10%. The pH of the reaction steadily decreases as the reaction proceeds and acids are formed. The final pH of the reaction mixture is generally in the range of from about 0 to about 5. The acid product may be produced at least in part in the form of its alkali metal salt and it is to be understood that the term "acid" as used in the specification and the appended claims is intended to include the salt form as well as the free acid form.

The process of the present invention is typically conducted under mild conditions, with good results being obtained using a temperature in the range of from about 0° C. to about 35° C., preferably about 5° C. to about 25° C., and most preferably, about 10° C. to about 20° C. Reaction pressures are not critical although higher pressures may result in increased reaction rates. Atmospheric pressures are typically used.

The process of the instant invention can be carried out either batchwise or continuously, using a stirrer equipped reactor or other well known contacting techniques to achieve adequate mixing. Preferred reaction conditions, e.g., temperature, pressure, addition rates, etc., vary somewhat depending on the specific nitroxide utilized and on the concentration of the nitroxide.

The process of the instant invention can be carried out in a variety of ways. For example, one equivalent of alkoxyalkanol, and 1,000 to 4,000 parts per million, basis nitroxide, of the resin-supported nitroxide, may be added to the reaction vessel, followed by the addition of two equivalents of chlorine-containing oxidant. Alternatively, one equivalent of alkoxyalkanol and two equivalents of a chlorine-containing oxidant and solvent may be added to the reaction vessel and allowed to reach equilibrium, followed by the dropwise or immediate addition of 1000–3,000 parts per million of the nitroxide which has been dissolved in a minimum amount of solvent. In a preferred embodiment, the reaction is carried out by adding the alkoxyalkanol, nitroxide and solvent together and then adding the chlorine-containing oxidant to the mixture. Following the reaction, the product may be separated from the supported catalyst by filtration. The reaction product can be purified by a number of conventional means such as high temperature water washing or extraction.

Depending upon process conditions and the nitroxide used, the selectivity to alkoxyalkanoic acids obtained by this invention can be greater than about 60%. The products produced by the instant process can be used as emulsifying agents or in a variety of detergent applications. For example, light duty dishwashing liquids, shampoos and heavy duty laundry liquids or powders.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The process of this invention will be further described by the following embodiments which are provided for illustration and are not to be construed as limiting the invention.

ILLUSTRATIVE EMBODIMENTS

In the following examples, the starting alkoxyalkanol was a NEODOL® Ethoxylate 23-3T alcohol which was prepared by ethoxylating a mixture of $C_{12}$ and $C_{13}$ substantially straight chain alcohols ($C_{12}:C_{13}$ 40:60) to an ethoxylated alcohol having about 3 ethylene oxide units per molecule and then topping off the unreacted alcohols and lower ethoxylates so that the final product contains less than about 5 percent unreacted alcohol.

The resin-supported nitroxide in the following examples was prepared by reacting 4-hydroxy-2,2,6,6-tetramethylpiperidin-1-oxyl and sodium hydride with a 1% cross-linked chloromethylated styrene/divinylbenzene copolymer containing 1 milliequivalent per gram (meq/g) of active chloride in the presence of dimethylformamide. After filtration and rinsing with dimethylformamide, the material was used in the following examples.

EXAMPLE 1

31.5 Grams of the starting alkoxyalkanol, 3 grams of the resin-supported nitroxide and 100 milliliters of dichloromethane were charged to a round bottomed flask. 6 Grams of sodium bicarbonate was added to 282 grams of 5.25% aqueous sodium hypochlorite. This solution was then added dropwise to the reaction mixture over a 1-hour period. The reaction temperature was maintained at 20° C. The reaction mixture was allowed to stir overnight at room temperature. The liquid phase was then removed from the solid supported nitroxide by filtration. The results are presented in Table I.

EXAMPLE 2

31.5 Grams of the starting alkoxyalkanol, 100 milliliters of dichloromethane and the resin-supported nitroxide recovered from Example 1 above were charged to a round bottomed flask. 6 Grams of sodium bicarbonate was added to 282 grams of 5.25% aqueous sodium hypochlorite. This solution was then added dropwise to the reaction mixture over a 1-hour period. The reaction temperature was maintained at 20° C. The reaction mixture was allowed to stir overnight at room temperature. The liquid phase was then removed from the solid supported nitroxide by filtration. The results are presented in Table I.

COMPARATIVE EXAMPLE A

Comparative Example A was carried out in a manner similar to Example 1 except that no resin-supported nitroxide was used. The results are presented in Table I.

COMPARATIVE EXAMPLE B

Comparative Example B was carried out in a manner similar to Example 1 except that no chlorine-containing oxidant was used. The results are presented in Table I.

As can be seen in Table I, both the resin-supported stable free radical nitroxide and chlorine-containing oxidant are necessary for the oxidation of the alkoxyalkanol to proceed. Example 2 shows that the resin-supported nitroxide can be recycled following previous use in an oxidative reaction.

TABLE I

| Oxidation of Alkoxyalkanols to Alkoxyalkanoic Acids | | | | |
|---|---|---|---|---|
| | % Conver. | % Sel. to Acids | % Sel. to Esters | % Sel. to Formates | % Sel. to Fatty Acids |
| Example 1 | 98 | 73 | 22 | 4 | 0.5 |
| Example 2 | 80 | 66 | 29 | 3.6 | 1.8 |
| Comparative Example A | 13 | 50 | 38 | 6 | 6 |
| Comparative Example B | 0 | 0 | 0 | 0 | 0 |

What is claimed is:

1. A process for the preparation of an alkoxyalkanoic acid of the formula

wherein R is a primary alkyl, secondary alkyl, tertiary alkyl, aromatic or an alkyl aromatic group having from 1 to about 1000 carbon atoms, R' is hydrogen or methyl or mixtures thereof (on the individual molecule) and n is an integer of from 1 to about 1000, which comprises reacting the corresponding alkoxyalkanol with a resin-supported stable free radical nitroxide having the formula:

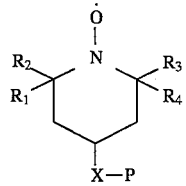

wherein (a) each of $R_1$, $R_2$, $R_3$, and $R_4$ is an alkyl, aryl or substituted alkyl group having 1 to about 15 carbon atoms, (b) X is selected from the group consisting of

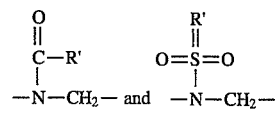

wherein R' alkyl, aryl, or amido, and P is a polystyrene, in the presence of a chlorine-containing oxidant and a solvent at a temperature in the range of from about 0° C. to about 100° C.

2. The process of claim 1 wherein P is a chloromethylated styrene/divinylbenzene copolymer.

3. The process of claim 1 wherein said chlorine-containing oxidant is selected from the group consisting of chlorine, hypochlorite, and N-chloro compounds.

4. The process of claim 3 wherein said chlorine-containing oxidant is selected from the group consisting of chlorine and hypochlorite.

5. The process of claim 1 wherein said solvent is selected from the group consisting of ethyl acetate, dichloromethane, acetonitrile, chlorobenzene, toluene, xylene, carbon tetrachloride, chloroform, dichloroethylene, tetrachloroethylene, diethyl ether, methyl-tert-butyl ether and mixtures thereof.

6. The process of claim 5 wherein said solvent is selected from the group consisting of ethyl acetate, dichloromethane and mixtures thereof.

7. The process of claim 1 wherein said alkoxyalkanol is contacted with said resin-supported stable free radical nitroxide, followed by the addition thereto of said chlorine-containing oxidant.

8. The process of claim 7 wherein the amount of resin-supported stable free radical nitroxide is in the range of from about 500 parts per million to about 30,000 parts per million, basis the weight of alkoxyalkanol.

9. The process of claim 8 wherein the amount of stable free radical nitroxide is in the range of from about 1,000 parts per million to about 10,000 parts per million, basis the weight of alkoxyalkanol.

10. The process of claim 7 wherein the amount of chlorine-containing oxidant is in the range of from about 2 equivalents to about 3 equivalents, basis the number of moles of alkoxyalkanol.

11. The process of claim 1 wherein said process is carried out at a temperature in the range of from about 5° C. to about 25° C. and at atmospheric pressure.

* * * * *